US008971570B1

(12) United States Patent
Raffle et al.

(10) Patent No.: US 8,971,570 B1
(45) Date of Patent: Mar. 3, 2015

(54) DUAL LED USAGE FOR GLINT DETECTION

(75) Inventors: Hayes Solos Raffle, Palo Alto, CA (US); Aaron Joseph Wheeler, San Francisco, CA (US)

(73) Assignee: Google Inc., Mountain View, CA (US)

(*) Notice: Subject to any disclaimer, the term of this patent is extended or adjusted under 35 U.S.C. 154(b) by 159 days.

(21) Appl. No.: 13/289,721

(22) Filed: Nov. 4, 2011

(51) Int. Cl.
*G06K 9/00* (2006.01)

(52) U.S. Cl.
USPC .................................................. 382/103

(58) Field of Classification Search
None
See application file for complete search history.

(56) References Cited

U.S. PATENT DOCUMENTS

| 5,016,282 | A | 5/1991 | Tomono et al. |
| 6,433,760 | B1* | 8/2002 | Vaissie et al. ............... 345/8 |
| 6,578,962 | B1 | 6/2003 | Amir |
| 7,401,920 | B1* | 7/2008 | Kranz et al. ................ 351/210 |
| 7,522,344 | B1 | 4/2009 | Curatu |
| 8,077,914 | B1* | 12/2011 | Kaplan ........................ 382/103 |
| 2002/0105482 | A1* | 8/2002 | Lemelson et al. .............. 345/7 |
| 2003/0098954 | A1 | 5/2003 | Amir et al. |
| 2003/0142041 | A1* | 7/2003 | Barlow et al. ................. 345/8 |
| 2004/0174496 | A1 | 9/2004 | Ji et al. |
| 2006/0110008 | A1 | 5/2006 | Vertegaal et al. |
| 2008/0267600 | A1* | 10/2008 | Omi ........................... 396/14 |
| 2011/0170060 | A1 | 7/2011 | Gordon |
| 2011/0228975 | A1* | 9/2011 | Hennessey et al. ........... 382/103 |

OTHER PUBLICATIONS

Hua, Video-based eyetracking methods and algorithms in head-mounted displays, Optics Express, May 15, 2006, 4328-4350, vol. 14, No. 10.
Curatu, Projection-based head-mounted display with eye-tracking capabilities, Proceedings of SPIE, 2005, 58750J-1-9, vol. 5875.

* cited by examiner

*Primary Examiner* — Atiba O Fitzpatrick
*Assistant Examiner* — Carol Wang
(74) *Attorney, Agent, or Firm* — McDonnell Boehnen Hulbert & Berghoff LLP (57) ABSTRACT

A wearable computing system may include an eye-tracking system configured to track the position of an eye of a wearer of the wearable computing system. In particular, an infrared light source illuminating the eye of a wearer at a relatively high intensity may generate specular reflections off the wearer's cornea, also called 'glints'. The glints can be imaged with an infrared camera. When the infrared light sources are illuminated at a relatively lower intensity, determination of the pupil location is possible. Glints, in combination with the pupil location, may be used to accurately determine the gaze direction and eye rotation. The determined gaze direction could be used in various eye-tracking applications. By controlling the light sources to change intensity levels and by combining multiple images of the eye to incorporate multiple glint locations with the pupil location, eye tracking can be performed with better accuracy and with fewer light sources.

27 Claims, 7 Drawing Sheets

DUAL LED USAGE FOR GLINT DETECTION

BACKGROUND

Wearable systems can integrate various elements, such as miniaturized computers, input devices, sensors, detectors, image displays, wireless communication devices as well as image and audio processors, into a device that can be worn by a user. Such devices provide a mobile and lightweight solution to communicating, computing and interacting with one's environment. With the advance of technologies associated with wearable systems and miniaturized optical elements, it has become possible to consider wearable compact optical displays that augment the wearer's experience of the real world.

By placing an image display element close to the wearer's eye(s), an artificial image can be made to overlay the wearer's view of the real world. Such image display elements are incorporated into systems also referred to as "near-eye displays", "head-mounted displays" (HMDs) or "heads-up displays" (HUDs). Depending upon the size of the display element and the distance to the wearer's eye, the artificial image may fill or nearly fill the wearer's field of view.

SUMMARY

In a first aspect, a method is provided. The method includes illuminating a viewing location during a first period of time with at least a first light source and a second light source, such that the first light source illuminates the viewing location with a higher intensity than the second light source. The method further includes acquiring a first image from light reflected from the viewing location during the first period of time. The method further includes illuminating the viewing location during a second period of time with at least the first light source and the second light source, such that the second light source illuminates the viewing location with a higher intensity than the first light source. The method further includes acquiring a second image from light reflected from the viewing location during the second period of time. The method further includes obtaining combined data from at least the first and second images. The combined data includes a reference location, a first glint location, and a second glint location. The method further includes determining a gaze direction based on the combined data.

In a second aspect, a wearable computing system is provided. The wearable computing system includes at least a first light source and a second light source. The first and the second light sources are configured to illuminate a viewing location during a first period of time, such that the first light source illuminates the viewing location with a higher intensity than the second light source. The first and the second light sources are further configured to illuminate the viewing location during a second period of time, such that the second light source illuminates the viewing location with a higher intensity than the first light source. The wearable computing system further includes a camera. The camera is configured to acquire a first image from light reflected from the viewing location during the first period of time. The camera is further configured to acquire a second image from light reflected from the viewing location during the second period of time. The wearable computing system also includes a computer. The computer is configured to obtain combined data from at least the first and the second images. The combined data includes a reference location, a first glint location, and a second glint location. The computer is further configured to determine a gaze direction based on the combined data.

In a third aspect, a non-transitory computer readable medium is provided. The non-transitory computer readable medium performs functions including controlling at least a first and a second light source to illuminate a viewing location during a first period of time, such that the first light source illuminates the viewing location with a higher intensity than the second light source. The non-transitory computer readable medium performs functions further including controlling a camera to acquire a first image from light reflected from the viewing location during the first period of time. The non-transitory computer readable medium performs functions further including controlling at least the first and the second light sources to illuminate the viewing location during a second period of time, such that the second light source illuminates the viewing location with a higher intensity than the first light source. The non-transitory computer readable medium performs functions further including controlling the camera to acquire a second image from light reflected from the viewing location during the second period of time. The non-transitory computer readable medium performs functions further including obtaining combined data from at least the first and the second images. The combined data includes a reference location, a first glint location, and a second glint location. The non-transitory computer readable medium performs functions further including determining a gaze direction based on the combined data.

In a fourth aspect, a method is provided. The method includes illuminating a viewing location during a first period of time using at least one light source, such that the at least one light source illuminates the viewing location at a first intensity. The method further includes acquiring a first image from light reflected from the viewing location during the first period of time. The method further includes illuminating the viewing location during a second period of time using the at least one light source, such that the at least one light source illuminates the viewing location at a second intensity. The second intensity is less than the first intensity. The method further includes acquiring a second image from light reflected from the viewing location during the second period of time. The method also includes obtaining combined data from at least the first and the second images. The combined data includes a reference location and a glint location. The method further includes determining a gaze direction based on the combined data.

DETAILED DESCRIPTION

In the following detailed description, reference is made to the accompanying figures, which form a part thereof. In the figures, similar symbols typically identify similar components, unless context dictates otherwise. The illustrative embodiments described in the detailed description and figures are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

1. Overview

A head-mounted display ("HMD") may enable its wearer to observe the wearer's real-world surroundings and also view a displayed image, such as a computer-generated image or virtual image. In some cases, the displayed image may overlay a portion of the wearer's field of view of the real world. Thus, while the wearer of the HMD is going about his or her daily activities, such as walking, driving, exercising, etc., the wearer may be able to see a displayed image generated by the HMD at the same time that the wearer is looking out at his or her real-world surroundings.

The displayed image might include, for example, graphics, text, and/or video. The content of the displayed image could relate to any number of contexts, including but not limited to the wearer's current environment, an activity in which the wearer is currently engaged, the biometric status of the wearer, and any audio, video, or textual communications that have been directed to the wearer. The images displayed by the HMD may also be part of an interactive user interface. For example, the HMD could be part of a wearable computing device. Thus, the images displayed by the HMD could include menus, selection boxes, navigation icons, or other user interface features that enable the wearer to invoke functions of the wearable computing device or otherwise interact with the wearable computing device.

The images displayed by the HMD could appear anywhere in the wearer's field of view. For example, the displayed image might occur at or near the center of the wearer's field of view, or the displayed image might be confined to the top, bottom, or a corner of the wearer's field of view. Alternatively, the displayed image might be at the periphery of or entirely outside of the wearer's normal field of view. For example, the displayed image might be positioned such that it is not visible when the wearer looks straight ahead but is visible when the wearer looks in a specific direction, such as up, down, or to one side. In addition, the displayed image might overlay only a small portion of the wearer's field of view, or the displayed image might fill most or all of the wearer's field of view. The displayed image could be displayed continuously or only at certain times (e.g., only when the wearer is engaged in certain activities).

The virtual images could be displayed based on the position and orientation of the HMD. For example, the HMD may include position and orientation sensors so that when the user moves his or her head, data regarding the position and orientation of the HMD can be received by a processor. The HMD may additionally include a display controllable by the processor, so when the user moves his or her head, the processor may adjust the displayed image on the display. In particular, the displayed image may move in the opposite direction of head movement to create the sensation of looking around a world with superimposed virtual images.

By incorporating an eye-tracking system into the HMD, the gaze direction of the HMD wearer may be determined. That is, the HMD may determine where the wearer of the HMD is looking. Further, the user may control the HMD and its associated user interface by eye movements. For example, the user may control the HMD by selecting various icons, text, graphical buttons, etc. that may be displayed within the display area as user interface content. By gazing fixedly at objects for a predetermined period of time, those objects may be selected. Various objects may act as input instructions that can cause the HMD computer to display, for instance, a different set of user interface content.

The eye-tracking system could include light sources such as infrared (IR) light-emitting diodes (LEDs). These LEDs may be configured to illuminate the eye(s) of the HMD wearer. Further, an infrared camera may be configured to acquire images of the eye location(s) of the HMD wearer. Depending upon at least the intensity level of the IR LEDs and the image exposure, a specular 'glint' image from a reflection off of the wearer's cornea may be generated. Alternatively, a more uniformly illuminated image of the eye pupil may be acquired. A controller could control multiple light sources to adjust their intensity levels throughout different periods of time and control a camera to capture an image of the viewing location during each period of time. Combined data based on the multiple images of the HMD wearer's eye(s) could include information such as the pupil location as well as multiple glint locations. Imaging the wearer's eye with multiple glints could provide for more accurate pupil tracking as well as better rotational determination. A computer could be used to, for example, determine the gaze direction of the HMD wearer from the combined data. As mentioned above, various functions of the HMD and/or the associated wearable computing system may be initiated using eye gaze.

Certain illustrative examples of a system and method for tracking eye movements are described below. It is to be understood, however, that other embodiments are possible and are implicitly considered within the context of the following example embodiments.

2. An Eye Tracking System with Dual Intensity-Level Light Sources

Figure 1:
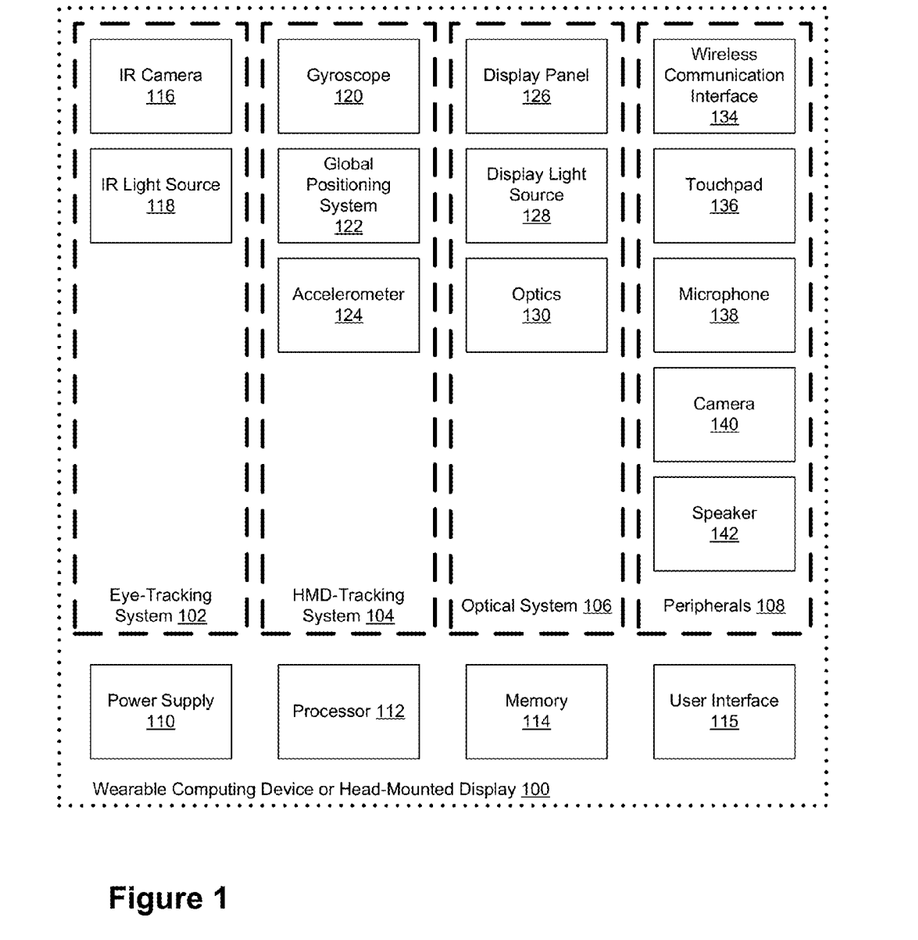
FIG. 1 is a schematic diagram of a wearable computing device, in accordance with an example embodiment.

FIG. 1 is a schematic diagram of a wearable computing device or a head-mounted display (HMD) 100 that may include several different components and subsystems. As shown, the HMD 100 includes an eye-tracking system 102, a HMD-tracking system 104, an optical system 106, peripherals 108, a power supply 110, a processor 112, a memory 114, and a user interface 115. The eye-tracking system 102 may include hardware such as an infrared camera 116 and at least one infrared light source 118. The HMD-tracking system 104 may include a gyroscope 120, a global positioning system (GPS) 122, and an accelerometer 124. The optical system 106 may include, in one embodiment, a display panel 126, a display light source 128, and optics 130. The peripherals 108 may include a wireless communication interface 134, a touchpad 136, a microphone 138, a camera 140, and a speaker 142.

In an example embodiment, HMD 100 includes a see-through display. Thus, the wearer of HMD 100 may observe a portion of the real-world environment, i.e., in a particular field of view provided by the optical system 106. In the example embodiment, HMD 100 is operable to display virtual images that are superimposed on the field of view, for example, to provide an "augmented reality" experience. Some of the virtual images displayed by HMD 100 may be superimposed over particular objects in the field of view. HMD 100 may also display images that appear to hover within the field of view instead of being associated with particular objects in the field of view.

Components of the HMD 100 may be configured to work in an interconnected fashion with other components within or outside their respective systems. For instance, in an example embodiment, the infrared camera 116 may image one or both of the HMD wearer's eyes. The infrared camera 116 may deliver image information to the processor 112, which may access the memory 114 and make a determination regarding the direction of the HMD wearer's gaze, or gaze direction. The processor 112 may further accept input from the GPS unit 122, the gyroscope 120, and/or the accelerometer 124 to determine the location and orientation of the HMD 100. Subsequently, the processor 112 may control the user interface 115 and the display panel 126 to display virtual images to the HMD wearer that may include context-specific information based on the HMD location and orientation as well as the HMD wearer's gaze direction.

HMD 100 could be configured as, for example, eyeglasses, goggles, a helmet, a hat, a visor, a headband, or in some other form that can be supported on or from the wearer's head. Further, HMD 100 may be configured to display images to both of the wearer's eyes, for example, using two see-through displays. Alternatively, HMD 100 may include only a single see-through display and may display images to only one of the wearer's eyes, either the left eye or the right eye. The HMD 100 may also represent an opaque display configured to display images to one or both of the wearer's eyes without a view of the real-world environment. Further, the HMD 100 could provide an opaque display for a first eye of the wearer as well as provide a view of the real-world environment for a second eye of the wearer.

A power supply 110 may provide power to various HMD components and could represent, for example, a rechargeable lithium-ion battery. Various other power supply materials and types known in the art are possible.

The functioning of the HMD 100 may be controlled by a processor 112 that executes instructions stored in a non-transitory computer readable medium, such as the memory 114. Thus, the processor 112 in combination with instructions stored in the memory 114 may function as a controller of HMD 100. As such, the processor 112 may control the user interface 115 to adjust the images displayed by HMD 100. The processor 112 may also control the wireless communication interface 134 and various other components of the HMD 100. The processor 112 may additionally represent a plurality of computing devices that may serve to control individual components or subsystems of the HMD 100 in a distributed fashion.

In addition to instructions that may be executed by the processor 112, the memory 114 may store data that may include a set of calibrated wearer eye pupil positions and a collection of past eye pupil positions. Thus, the memory 114 may function as a database of information related to gaze direction. Such information may be used by HMD 100 to anticipate where the user will look and determine what images are to be displayed to the wearer. Calibrated wearer eye pupil positions may include, for instance, information regarding the extents or range of the wearer's eye pupil movement (right/left and upwards/downwards) as well as wearer eye pupil positions that may relate to various reference axes.

Reference axes could represent, for example, an axis extending from a viewing location and through a target object or the apparent center of a field of view (i.e. a central axis that may project through a center point of the apparent display panel of the HMD). Other possibilities for reference axes exist. Thus, a reference axis may further represent a basis for determining dynamic gaze direction.

In addition, information may be stored in the memory 114 regarding possible control instructions that may be enacted using eye movements. For instance, two consecutive wearer eye blinks may represent a control instruction directing the HMD 100 to capture an image using camera 140. Another possible embodiment may include a configuration such that specific eye movements may represent a control instruction. For example, a HMD wearer may lock or unlock the user interface 115 with a series of predetermined eye movements.

Control instructions could be based on dwell-based selection of a target object. For instance, if a wearer fixates visually upon a particular virtual image or real-world object for longer than a predetermined time period, a control instruction may be generated to select the virtual image or real-world object as a target object. Many other control instructions are possible.

The HMD 100 may include a user interface 115 for providing information to the wearer or receiving input from the wearer. The user interface 115 could be associated with, for example, the displayed virtual images and/or one or more input devices in peripherals 108, such as touchpad 136 or microphone 138. The processor 112 may control the functioning of the HMD 100 based on inputs received through the user interface 115. For example, the processor 112 may utilize user input from the user interface 115 to control how the HMD 100 displays images within a field of view or to determine what images the HMD 100 displays.

An eye-tracking system 102 may be included in the HMD 100. In an example embodiment, an eye-tracking system 102 may deliver information to the processor 112 regarding the eye position of a wearer of the HMD 100. The eye-tracking data could be used, for instance, to determine a direction in which the HMD wearer may be gazing. The processor 112 could determine target objects among the displayed images based on information from the eye-tracking system 102. The processor 112 may control the user interface 115 and the display panel 126 to adjust the target object and/or other displayed images in various ways. For instance, a HMD wearer could interact with a mobile-type menu-driven user interface using eye gaze movements.

The infrared camera 116 may be utilized by the eye-tracking system 102 to capture images of a viewing location associated with the HMD 100. Thus, the infrared camera 116 may image the eye of a HMD wearer that may be located at the viewing location. The images could be either video images or still images. The images obtained by the infrared camera 116 regarding the HMD wearer's eye may help determine where the wearer is looking within the HMD field of view, for instance by allowing the processor 112 to ascertain the location of the HMD wearer's eye pupil. Analysis of the images obtained by the infrared camera 116 could be performed by the processor 112 in conjunction with the memory 114 to determine, for example, a gaze direction.

The imaging of the viewing location could occur continuously or at discrete times depending upon, for instance, user interactions with the user interface 115 and/or the state of the infrared light source 118 which may serve to illuminate the viewing location. The infrared camera 116 could be integrated into the optical system 106 or mounted on the HMD 100. Alternatively, the infrared camera could be positioned apart from the HMD 100 altogether. Furthermore, the infrared camera 116 could additionally represent a conventional visible light camera with sensing capabilities in the infrared wavelengths. The infrared camera 116 could be operated at video rate frequency (e.g. 60 Hz) or a multiple of video rates (e.g. 240 Hz), which may be more amenable to combining multiple frames while determining a gaze direction.

The infrared light source 118 could represent one or more infrared light-emitting diodes (LEDs) or infrared laser diodes that may illuminate a viewing location. One or both eyes of a wearer of the HMD 100 may be illuminated by the infrared light source 118. The infrared light source 118 may be positioned along an optical axis common to the infrared camera, and/or the infrared light source 118 may be positioned elsewhere. The infrared light source 118 may illuminate the viewing location continuously or may be turned on at discrete times. Additionally, when illuminated, the infrared light source 118 may be modulated at a particular frequency. Other types of modulation of the infrared light source 118, such as adjusting the intensity level of the infrared light source 118, are possible.

The eye-tracking system 102 could be configured to acquire images of glint reflections from the outer surface of the cornea, which are also called first Purkinje images. Alternatively, the eye-tracking system 102 could be configured to acquire images of reflections from the inner, posterior surface of the lens, which are termed fourth Purkinje images. In yet another embodiment, the eye-tracking system 102 could be configured to acquire images of the eye pupil with so-called bright and/or dark pupil images. In practice, a combination of these glint and pupil imaging techniques may be used for rotational eye tracking, accuracy, and redundancy. Other imaging and tracking methods are possible. Those knowledgeable in the art will understand that there are several alternative ways to achieve eye tracking with a combination of infrared illuminator and camera hardware.

The HMD-tracking system 104 could be configured to provide a HMD position and a HMD orientation to the processor 112. This position and orientation data may help determine a central axis to which a gaze direction is compared. For instance, the central axis may correspond to the orientation of the HMD.

The gyroscope 120 could be a microelectromechanical system (MEMS) gyroscope, a fiber optic gyroscope, or another type of gyroscope known in the art. The gyroscope 120 may be configured to provide orientation information to the processor 112. The GPS unit 122 could be a receiver that obtains clock and other signals from GPS satellites and may be configured to provide real-time location information to the processor 112. The HMD-tracking system 104 could further include an accelerometer 124 configured to provide motion input data to the processor 112.

The optical system 106 could include components configured to provide virtual images at a viewing location. The viewing location may correspond to the location of one or both eyes of a wearer of a HMD 100. The components could include a display panel 126, a display light source 128, and optics 130. These components may be optically and/or electrically-coupled to one another and may be configured to provide viewable images at a viewing location. As mentioned above, one or two optical systems 106 could be provided in a HMD apparatus. In other words, the HMD wearer could view virtual images in one or both eyes, as provided by one or more optical systems 106. Also, as described above, the optical system(s) 106 could include an opaque display and/or a see-through display, which may allow a view of the real-world environment while providing superimposed virtual images.

Various peripheral devices 108 may be included in the HMD 100 and may serve to provide information to and from a wearer of the HMD 100. In one example, the HMD 100 may include a wireless communication interface 134 for wirelessly communicating with one or more devices directly or via a communication network. For example, wireless communication interface 134 could use 3G cellular communication, such as CDMA, EVDO, GSM/GPRS, or 4G cellular communication, such as WiMAX or LTE. Alternatively, wireless communication interface 134 could communicate with a wireless local area network (WLAN), for example, using WiFi. In some embodiments, wireless communication interface 134 could communicate directly with a device, for example, using an infrared link, Bluetooth, or ZigBee. The wireless communication interface 134 could interact with devices that may include, for example, components of the HMD 100 and/or externally-located devices.

Although FIG. 1 shows various components of the HMD 100 (i.e., wireless communication interface 134, processor 112, memory 114, infrared camera 116, display panel 126, GPS 122, and user interface 115) as being integrated into HMD 100, one or more of these components could be physically separate from HMD 100. For example, the infrared camera 116 could be mounted on the wearer separate from HMD 100. Thus, the HMD 100 could be part of a wearable computing device in the form of separate devices that can be worn on or carried by the wearer. The separate components that make up the wearable computing device could be communicatively coupled together in either a wired or wireless fashion.

Figure 2A:
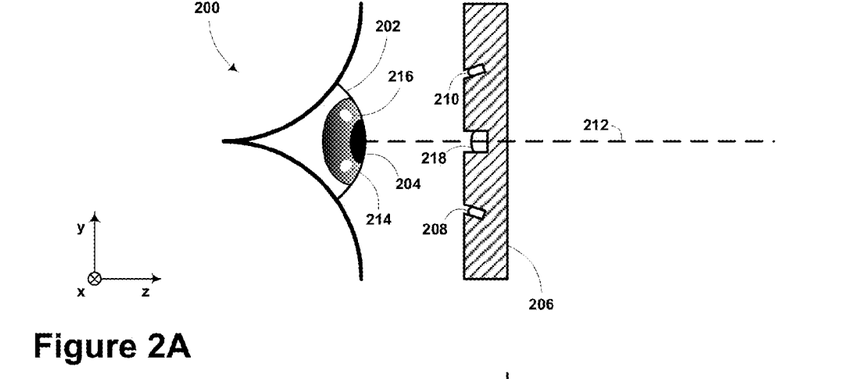
FIG. 2A is a side view of an eye-tracking system, in accordance with an example embodiment.
Figure 2B:
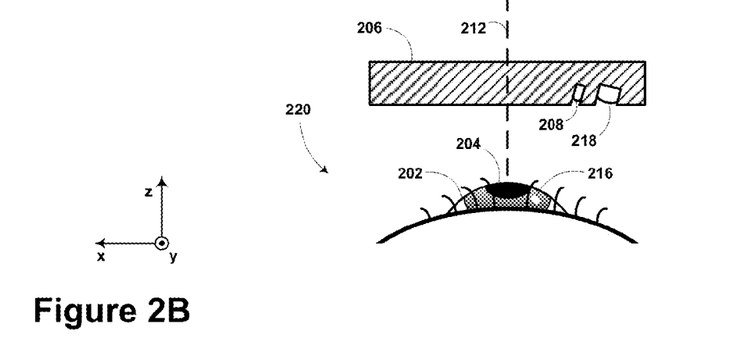
FIG. 2B is a top view of the eye-tracking system of FIG. 2A, in accordance with an example embodiment.
Figure 2C:
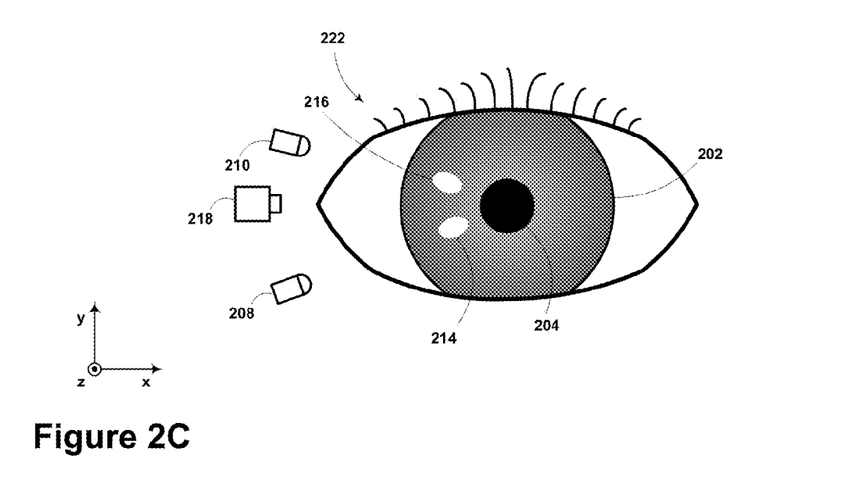
FIG. 2C is a front view of the eye-tracking system of FIG. 2A and FIG. 2B, in accordance with an example embodiment.

FIGS. 2A, 2B, and 2C show side, top and front views of an eye-tracking system (200, 220, and 222) that may include an eye 202 of a HMD wearer, an eye pupil 204, and a substrate 206. The substrate 206 could include an at least partially transparent optical material such as glass or plastic that could permit the HMD wearer to observe the real-world environment. Additionally, the substrate 206 could be part of a display configured to display a virtual image to the HMD wearer. Alternatively, the substrate 206 could be opaque. The substrate 206 could act as an attachment location for various light sources 208 and 210 as well as a camera 218. The light sources 208 and 210 could be infrared or visible light-emitting diodes (LEDs). Infrared LEDs with a small size may be implemented, such as the Vishay Technology TSML 1000 product. Other light source types are possible, such as laser diodes. The camera 218 could be a camera configured to at least image light from the light sources 208 and 210 as reflected from the HMD wearer's eye 202. For instance, the camera 218 could be an infrared camera.

The light sources 208 and 210 may produce glint reflections from the eye 202 that may appear as bright glints 214 and 216, respectively, in the wavelength range of illumination. The camera 218 may image the eye 202, the eye pupil 204, and glints 214 and 216. Upon imaging of the eye 202, image processing can be conducted with a processor 112 in order to determine, for instance, the extents and centroid location of the person's pupil. These pupil extents and/or the pupil centroid location may help determine an eye gaze direction 212.

The number of light sources like light sources 208 and 210 may vary. It is possible to conduct eye-tracking with one light source. Further, using more light sources could offer some redundancy to the eye-tracking process. Camera 218 could represent more than one camera depending on the particular embodiment.

Other possibilities for eye-tracking exist that may determine different reference points on the eye and may be implemented within the context of this invention. For instance, instead of ascertaining the pupil centroid to determine the gaze direction, position data from multiple glint reflections on the eye may be used in addition to or in lieu of information about the pupil position to determine the gaze direction. For instance, dark pupil tracking could be used instead of the Purkinje technique detailed herein. Alternatively, the centroid of the limbus (the ring that connects the inner, colored cornea and the outer, white sclera) could be determined instead of or in addition to the pupil of the eye 204.

The camera 218 may selectively filter and detect the infrared light from the combination of visible and infrared light to obtain information regarding the wearer's eye pupil location. Alternatively and/or additionally, the light sources 208 and 210 may be modulated with respect to a clock signal of a lock-in amplifier or phase-locked loop in order that the light signal is transduced efficiently.

Although FIGS. 2A and 2B depict the light sources 208 and 210 as well as the camera 218 embedded in the substrate 206, those skilled in the art will understand that other mounting locations for these elements are possible as well. For instance, it may be advantageous to obtain images of the eye pupil using light sources that illuminate the eye from positions off-axis and/or on-axis with respect to the gaze direction 212. Therefore, the light sources 210 and 208 may represent one or more LEDs located at different locations in, and/or separate from, the substrate 206.

Similarly, reflected infrared light may be collected from off-axis angles, and thus the camera 218 may also be located elsewhere on the substrate 206 or located separately from the substrate 206. Those with skill in the art will understand that there are other variations of transducing an infrared light signal mixed with a visible light signal with an infrared camera and that those variations are included implicitly in this specification.

Figure 3A:
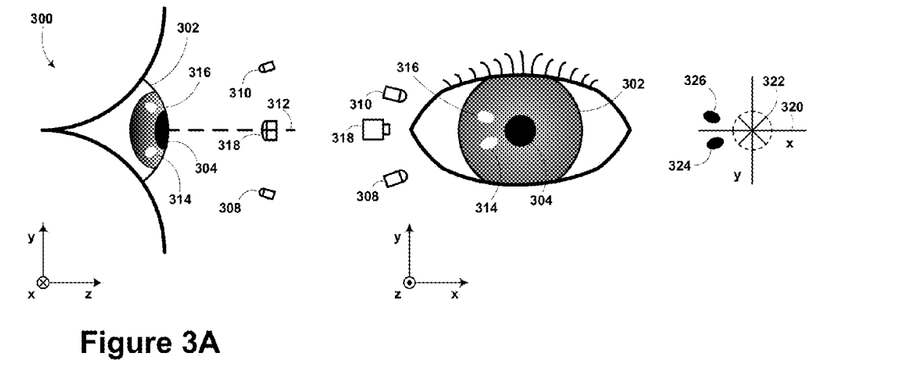
FIG. 3A is a side view of an eye-tracking system with a forward gaze direction, in accordance with an example embodiment.
Figure 3B:
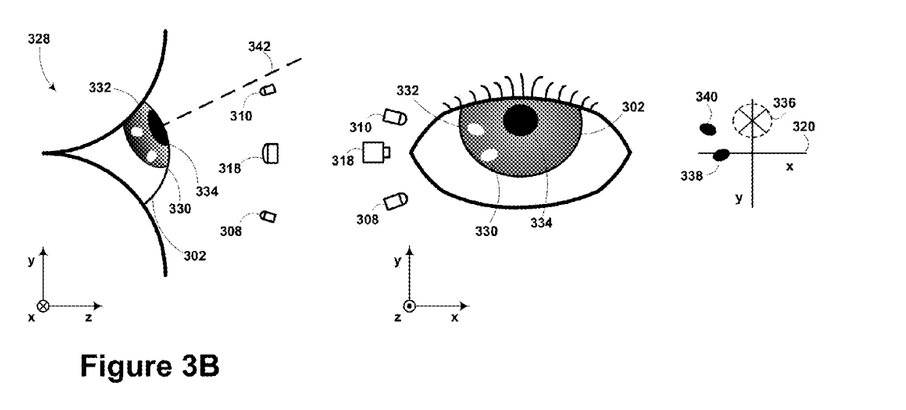
FIG. 3B is a side view of the eye-tracking system of FIG. 3A with an upward gaze direction, in accordance with an example embodiment.

FIGS. 3A and 3B are side and front views of an eye of a HMD user gazing forward and gazing upward, respectively. In the former situation, when a HMD user may be gazing forward 300, light sources 308 and 310 could be configured to illuminate the HMD user's eye 302. Glint reflections 314 and 316 from the HMD user's eye 302 could be generated based on the illumination from the light sources 308 and 310. These glint reflections 314 and 316 could be first Purkinje images from reflections from the outer surface of the HMD user's cornea. The glint reflections 314 and 316 as well as the eye pupil 304 could be imaged by a camera 318. Images could be sent to a processor that may, in turn, analyze the glint locations 324 and 326 with respect to a coordinate system 320 in order to determine and/or confirm a pupil location 322. In the case where the HMD user may be gazing forward, the pupil location may be determined to be near the center of the reference coordinate system 320. Accordingly, a gaze direction 312 may be determined to be straight ahead. A gaze point may be determined to be at a point along the gaze direction 312.

FIG. 3B depicts a situation 328 where a HMD user is gazing upward. Similar to the aforementioned example, light sources 308 and 310 could induce respective glint reflections 330 and 332 from the HMD user's eye 302. In this situation, however, the glint reflections 330 and 332 may appear in different locations due to the change in the eye gaze direction of the HMD wearer and asymmetry of the shape of the eye 302. Thus glint reflections 338 and 340 may move with respect to reference coordinate system 320. Image analysis could be used to determine the pupil location 336 within the reference coordinate system 320. From the pupil location 336, a gaze direction 342 may be determined. A gaze point could be determined as a point along the gaze direction 342.

Figure 3C:
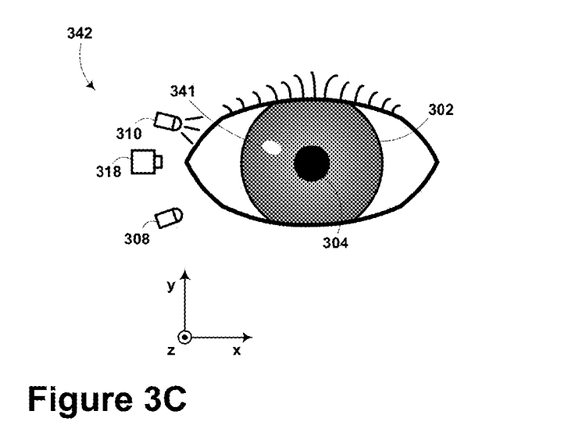
FIG. 3C is a side view of the eye-tracking system of FIGS. 3A and 3B with a forward gaze direction during a first period of time, in accordance with an example embodiment.

FIG. 3C illustrates a situation 342 where a user of a HMD may be looking forward during a first period of time. Light sources 308 and 310 could be illuminating a viewing location, which may correspond with the HMD user's eye 302. Specifically, light source 310 could be illuminating the viewing location at a higher intensity compared to light source 308. The ratio between illumination intensities could be as much as infinity (one light source could provide zero intensity, while the other provides non-zero intensity) or any smaller ratio such that the difference is resolvable by at least the combination of camera 318 and image recognition software. Accordingly, a first image acquired by camera 318 during this first period of time may include a more prominent first Purkinje image, or glint 341, which may be due to a corneal reflex reflection from light source 310. Thus, the first image may include information regarding the eye pupil 304 as well as a first glint 341. In other embodiments, multiple glints could be imaged during the first period of time with each glint exhibiting a similar or a different intensity.

Figure 3D:
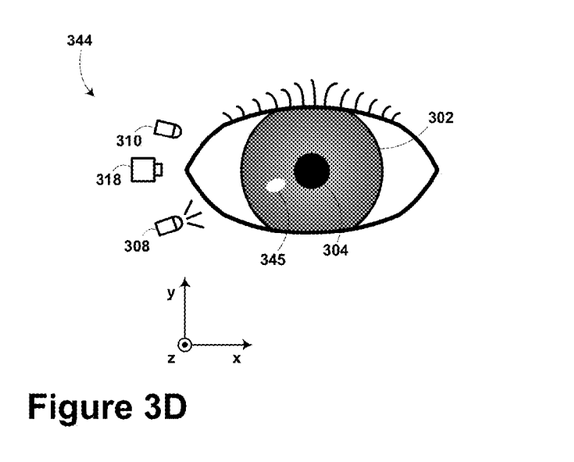
FIG. 3D is a side view of the eye-tracking system of FIGS. 3A, 3B, and 3C with a forward gaze direction during a second period of time, in accordance with an example embodiment.

FIG. 3D presents a situation 344 in which a user of a HMD may be looking forward during a second period of time. Similar to FIG. 3C, light sources 308 and 310 could illuminate the viewing location/eye 302. However, in this situation 344, light source 308 could be illuminating the viewing location with a higher intensity than light source 310. The higher intensity illumination from light source 308 could generate a corneal reflex reflection which may be second glint 345. Correspondingly, the second glint 345 could be visible in a second image captured by camera 318 during the second period of time. Information in the second image could include the eye pupil 304 as well as the second glint 345. In other embodiments, multiple glints could be imaged during the second period of time with each glint exhibiting a similar or a different intensity.

Figure 3E:
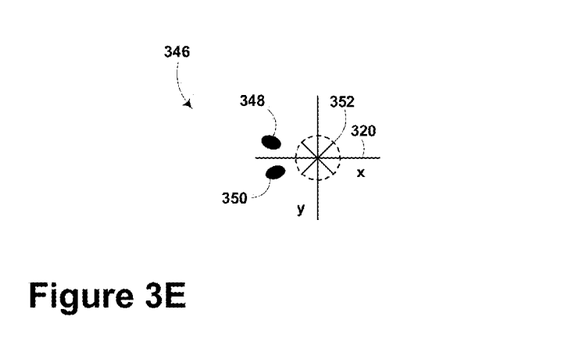
FIG. 3E is a graph of the combined data obtained from FIGS. 3C and 3D, in accordance with an example embodiment.

FIG. 3E illustrates combined data 346 which may include information combined from at least the first and the second images. Such combined data 346 could be combined by processor 112 and could be represented in a graphical or other form. Accordingly, first glint location 348, second glint location 350, and pupil location 352 could be included in the combined data 346. The combined data 346 could be used by processor 112, for instance, to ascertain a gaze direction of a HMD wearer. The combined data 346 could be updated dynamically and could also include more than two images. For example, combined data 346 could combine more than two images, each of which could include more or less than a single glint in the image. For instance, it may be possible to combine a 'pupil' image with two 'glint' images to obtain a combined image with all three elements. The combined data may also include information from other systems associated with or remote from the HMD 100. For example, the combined data may include information about HMD movement, for instance to compensate for head movement between the combined images. Many other forms of combined data are possible. Thus, obtaining combined data 346 with light sources that can change illumination intensity levels may allow gaze direction acquisition with fewer light sources and better rotational accuracy than other techniques.

Figure 4A:
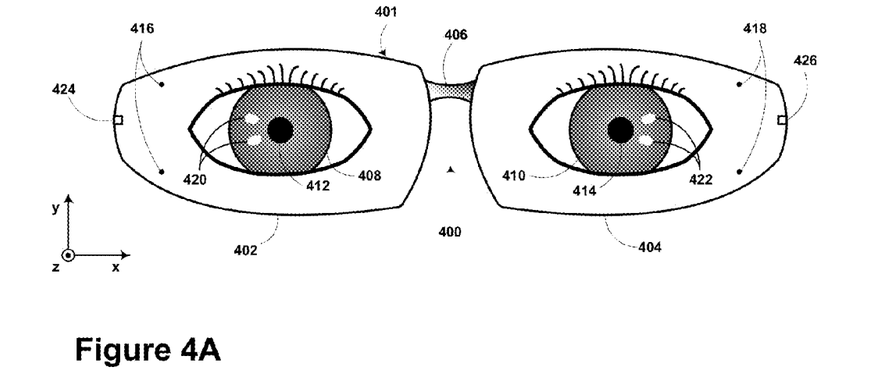
FIG. 4A is a front view of a head-mounted display, in accordance with an example embodiment.
Figure 4B:
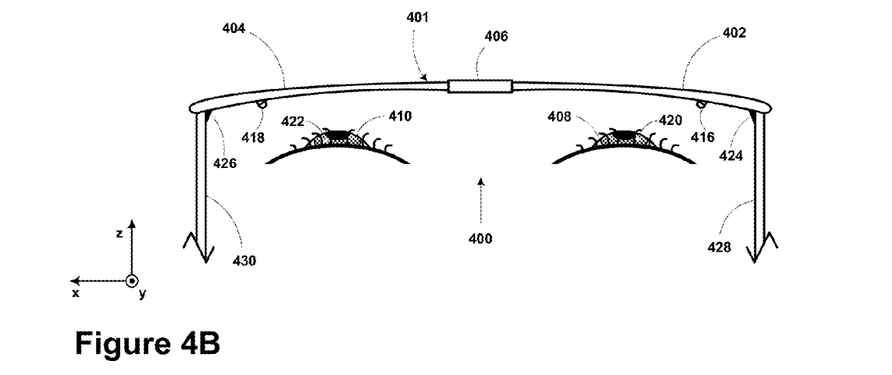
FIG. 4B is a top view of the head-mounted display of FIG. 4A, in accordance with an example embodiment.
Figure 4C:
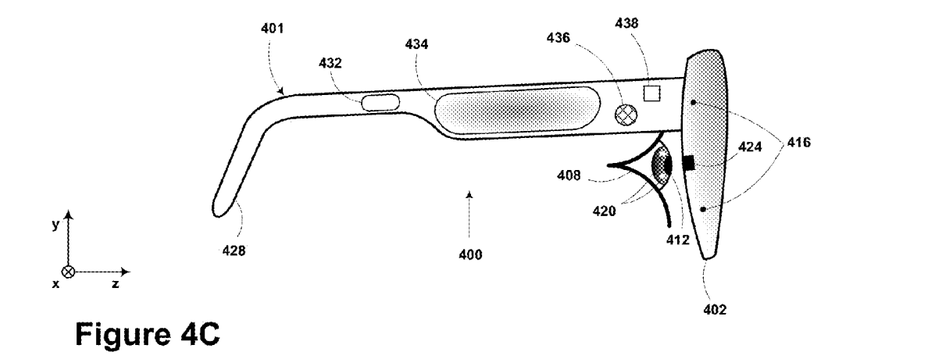
FIG. 4C is a side view of the head-mounted display of FIG. 4A and FIG. 4B, in accordance with an example embodiment.

FIG. 4A presents a front view of a head-mounted display (HMD) 400 in an example embodiment that includes a head-mounted support 401. FIGS. 4B and 4C present the top and side views, respectively, of the HMD in FIG. 4A. Although this example embodiment is provided in an eyeglasses format, it will be understood that wearable systems and HMDs may take other forms, such as hats, goggles, masks, headbands and helmets. The head-mounted support 401 includes a center frame support 406, lens elements 402 and 404, and extending side-arms 428 and 430. The center frame support 406 and side-arms 428 and 430 are configured to secure the head-mounted support 401 to the wearer's head via the wearer's nose and ears, respectively. The center frame support 406 and the extending side-arms 428 and 430 may be formed of a solid structure of plastic or metal, or may be formed of a hollow structure of similar material so as to allow wiring and component interconnects to be internally routed through the head-mounted support 401. Alternatively or additionally, head-mounted support 401 may support external wiring. Lens elements 402 and 404 are at least partially transparent so as to allow the wearer to look through them. In particular, the wearer's left eye 410 may look through left lens 404 and the wearer's right eye 408 may look through right lens 402. One or more optical systems configured to display images to a HMD wearer could be incorporated into or associated with the right lens 402 and the left lens 404 so that the HMD wearer could observe overlaid virtual images on a field of view of the real-world environment. Alternatively, optical systems could be mounted separate from the lens elements 402 and 404. Other ways of using optical systems for use as heads up displays (HUDs) or HMDs are known in the art and are considered implicitly herein.

Although this example embodiment includes an optical system for each of the wearer's eyes, it is to be understood that a HMD might include an optical system for only one of the wearer's eyes (either left eye 410 or right eye 408). The HMD 400 may include various elements such as a processor 432, a touchpad 434, a microphone 436, and a button 438. The processor 432 may use data from, among other sources, various sensors and cameras to determine the virtual image that should be displayed to the user.

In an example embodiment, as described earlier, a light source or sources (416 and 418) may illuminate the viewing location(s) 408 and 410, i.e. the wearer's eye(s), and the reflected infrared light may include glints 420 and 422, which may be collected and imaged with cameras 424 and 426. The images of glints 420 and 422 may be transmitted to processor 432, which may accordingly determine a gaze direction of a wearer of the HMD from the relative and absolute locations of the glints 420 and 422. The gaze direction may correspond to where the HMD wearer may be looking Gaze point locations could be further determined by, for instance, the intersection of the physical or apparent display area and the gaze direction. These gaze point locations (or more directly, gaze locations) may be used by the processor 432 to determine input instructions that could correspond to various functions, for instance, to adjust the displayed content in the display area of the HMD.

Thus, light sources 416 and 418, cameras 424 and 426, and processor 432 may function as a gaze-acquisition system for determining gaze directions from images acquired by cameras 424 and 426 and for determining gaze locations based on where the gaze directions intersect the display. Additionally, depending upon the particular embodiment, it may be the case that a gaze-acquisition system is made available to one eye of the HMD wearer and not to both eyes of the HMD wearer.

Those skilled in the art will understand that other user input devices, user output devices, wireless communication devices, sensors, and cameras may be reasonably included in such a wearable computing system.

Other embodiments could include the use of different eye gaze determination techniques. For instance, instead of using the eye pupil to determine gaze direction, it is possible to track eye motions using the boundary between the sclera and iris (408 and 410 in FIGS. 4A and 4B). For the purposes of determining an eye gaze direction, finding the centroid of the sclera/iris boundary (also called the limbus) may be equivalent to finding the centroid of a pupil.

Other possibilities for eye-tracking exist that may determine different reference points on the eye and may be implemented within the context of this invention. For instance, instead of ascertaining the pupil centroid to determine the gaze direction, position data from multiple glint reflections on the eye may be used in addition to or in lieu of information about the pupil position to determine the gaze direction.

Figure 5:
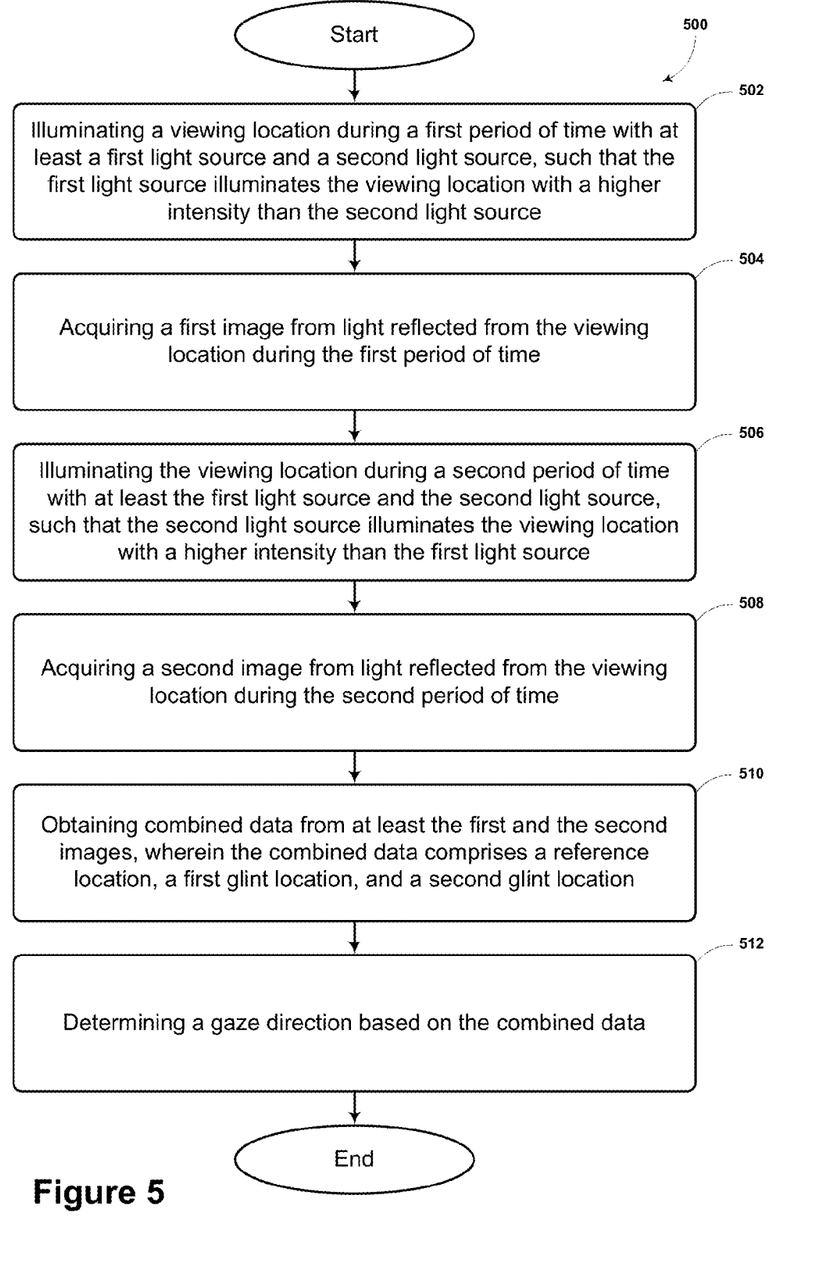
FIG. 5 is a flowchart of a method, in accordance with an example embodiment.

3. A Method for Eye Tracking Using Light Sources with Adjustable Intensity Levels A method 500 is provided for using an eye tracking system with multiple light sources and adjustable illumination intensity levels to determine gaze direction. The method could be performed using an apparatus shown in FIGS. 1-4C and as described above, however, other configurations could be used. FIG. 5 illustrates the steps in an example method, however, it is understood that in other embodiments, the steps may appear in different order and steps may be added or subtracted.

Step 502 includes illuminating a viewing location during a first period of time with at least a first light source and a second light source. The viewing location could correspond with a HMD wearer's eye 302 as shown in FIG. 3C. The first and the second light sources could be infrared light-emitting diodes (LEDs). During the first period of time, the first light source illuminates the viewing location at a higher intensity than the second light source.

Step 504 includes acquiring a first image from light reflected from the viewing location during the first period of time. The first image may include information regarding a first glint 341 generated from a corneal reflex reflection of the first light source as well as an eye pupil 304. The image may be acquired using an infrared camera and the image exposure could represent the entire first period of time.

Step 506 includes illuminating the viewing location during a second period of time with at least the first and second light sources. The second light source illuminates the viewing location with a higher intensity than the first light source as shown in FIG. 3D.

Step 508 includes acquiring a second image from light reflected from the viewing location during the second period of time. The second image may include information regarding a second glint 345 generated from a corneal reflex reflection of the second light source as well as an eye pupil 304.

Step 510 includes obtaining combined data from at least the first and second images. The data from the first and the second images could be combined by processor 112 and image processing software, for example. The combined data includes a reference location, as well as first and second glint locations (324 and 326). In the example embodiment, the reference location could represent the location of a centroid of an eye pupil 322. The combined data could be used to ascertain the pupil location and rotation.

Step 512 includes the determination of a gaze direction based on the combined data. For example, processor 112 and memory 114 could determine a gaze direction based on a pupil location/rotation map.

The aforementioned method could be performed with more than two light sources. For instance, four light sources could be used in a similar embodiment. In such an embodiment, the four light sources could be mounted to the HMD and arranged in a 'diamond' pattern. The diamond pattern could be centered on the HMD user's eye or both eyes. Each of the four light sources could be illuminated during different time periods. Alternatively, various combinations of the four light sources could be illuminated at the same time during various time periods. In one embodiment, each light source could be illuminated in turn in a clockwise or counterclockwise fashion around the diamond pattern. Alternatively, in each image frame, one of the infrared LEDs could be turned off. The three remaining light sources may provide global illumination. In this manner, glints may be distinguished from ambient noise. Other illumination timing patterns are possible.

Further, the light sources could vary in illumination intensity when illuminated. Thus, images of the viewing location (the HMD user's eye or eyes) could feature glints corresponding to illumination from one or more light sources. Also, the size, the intensity, and/or the lack of glints in the plurality of images acquired by processor 112 may serve to more easily and reliably determine the pupil location of the HMD user. Thus, using four light sources, it may be possible to perform the aforementioned method 500. In practice, the use of more than two light sources may also provide more uniform illumination of the HMD user's eye(s) as compared to one or two light source illumination. Other embodiments are possible; in fact, similar methods and apparatuses to those described herein could be realized with any number of light sources equal to or greater than one.

Figure 6:
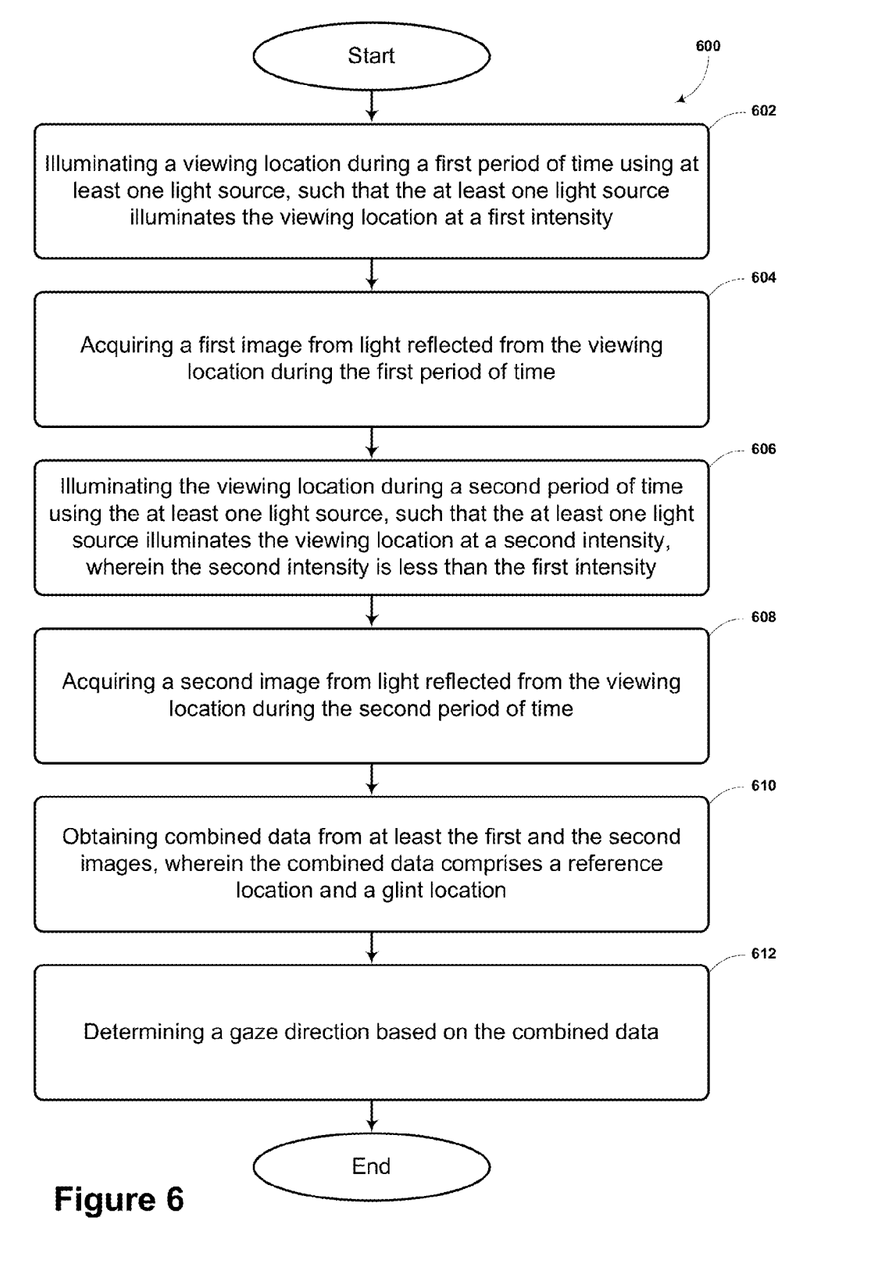
FIG. 6 is a flowchart of a method, in accordance with an example embodiment

4. A Method for Eye Tracking Using a Single Light Source with Adjustable Intensity Levels A method 600 is provided for using an eye tracking system with at least a single light source with adjustable illumination intensity levels to determine gaze direction. This method is similar to the aforementioned method 500 that involves multiple light sources to achieve eye tracking with adjustable intensity levels. However, it is also possible to perform eye tracking using one light source by varying the intensity level of the light source. The method could be performed using an apparatus shown in FIGS. 1-4C and as described above, however, other configurations could be used. FIG. 6 illustrates the steps in an example method, however, it is understood that in other embodiments, the steps may appear in different order and steps may be added or subtracted.

Method step 602 involves illuminating a viewing location (which could correspond to a HMD user's eye) with at least one light source at a first intensity during a first period of time. As described in previous embodiments, the light source could be an infrared LED. In an example embodiment, a single light source could be located on or off-axis with respect to the camera axis. Method step 604 includes acquiring a first image of the light reflected from the viewing location during the first period of time. The image could be acquired using an infrared camera.

Method step 606 includes illuminating the viewing location with at least one light source during a second period of time with a second intensity. In the example embodiment, the single light source could illuminate the viewing location at a lower intensity than during the first period of time. Method step 608 includes acquiring a second image from light reflected from the viewing location during the second period of time.

Method step 610 includes obtaining combined data from at least the first and second images. The combined data includes a reference location (which could be the location of the pupil of the HMD wearer's eye) as well as a glint location, which, in the example embodiment, may be generated due to a specular reflection off the cornea of an eye from the single light source. The glint and reference location could be used to determine a gaze direction, as recited in method step 612.

Although this method specifically includes light sources, such as infrared LEDs, that may generate reflective glints off the eye of the HMD user, ambient light may additionally be employed to aid in imaging the HMD user's eye. For instance, ambient light from the sun or other light sources within the environment of the HMD could illuminate the HMD user's eye(s). These ambient light sources could provide at least partial illumination in the first and second images acquired in method steps 604 and 608.

These ambient light sources may also produce glints that are visible in the acquired images. Nonetheless, the intended glint may be distinguished from any ambient glints by comparing the first image acquired in step 604 with the second image acquired in step 608. In particular, the intended glint will be less intense (or perhaps not visible at all) in the second image, because the light source that creates the intended glint illuminates the viewing location at a lower intensity during the second period of time, whereas ambient glints will generally have about the same intensity in the first and second images. Thus, a glint that appears in the first image but appears more dimly in the second image, or is absent in the second image, may be identified as the intended glint.

In another example embodiment, in addition to the aforementioned steps of method 600, a third image could be acquired from light reflected from the viewing location during a third period of time. The third image may include an image of the viewing location while the at least one light source is not illuminating the viewing location. For instance, the third image could be captured while the infrared LED is off. This third image could be combined with the first and second images to form the combined data from which a gaze direction may be determined. By capturing an image while the infrared LED is off, it may be possible to provide a better signal to noise ratio for forming the combined data. For example, since the at least one light source is off when the third image is acquired, the third image can be used to further distinguish between an intended glint and any ambient glints.

5. A Non-Transitory Computer Readable Medium for Eye Tracking with Adjustable Intensity Light Sources Some or all of the functions described above and illustrated in FIGS. 3C, 3D, 3E, and 5 may be performed by a computing device in response to the execution of instructions stored in a non-transitory computer readable medium. The non-transitory computer readable medium could be, for example, a random access memory (RAM), a read-only memory (ROM), a flash memory, a cache memory, one or more magnetically encoded discs, one or more optically encoded discs, or any other form of non-transitory data storage. The non-transitory computer readable medium could also be distributed among multiple data storage elements, which could be remotely located from each other. The computing device that executes the stored instructions could be a wearable computing device, such as a wearable computing device 100 illustrated in FIG. 1. Alternatively, the computing device that executes the stored instructions could be another computing device, such as a server in a server network.

The non-transitory computer readable medium may store instructions executable by the processor 112 to perform various functions. For instance, the processor 112 may be instructed to control a first and a second light source 118 to illuminate a viewing location, which may correspond to the HMD wearer's eye(s), during a first period of time. Furthermore, the processor 112 may adjust the intensity levels for the respective light sources 118 such that the first light source illuminates the viewing location at a higher intensity than the second light source. The intensity levels of the respective light sources 118 could be controlled by adjusting the amount of electrical power delivered to each light source, for example. Other ways of adjusting and/or modulating light intensity levels from an infrared light-emitting diode are implicitly contemplated herein. During the first period of time, the processor 112 may further control the camera 116 to acquire a first image from light reflected from the viewing location.

The non-transitory computer readable medium may further include instructions executable by the processor 112 to carry out functions such as controlling the first and the second light sources 118 to illuminate the viewing location during a second period of time, such that the second light source illuminates the viewing location with a higher intensity than the first light source. Similar to the first period of time, the processor 112 could control a camera 116 to acquire a second image from light reflected from the viewing location during the second period of time.

The non-transitory computer readable medium may instruct the processor 112 to carry out further functions such as obtaining combined data from at least the first and second images to include a reference location as well as first and second glint locations. Based upon the combined data, a gaze direction may be determined by the processor 112.

CONCLUSION

The above detailed description describes various features and functions of the disclosed systems, devices, and methods with reference to the accompanying figures. While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method, comprising:
   illuminating a viewing location during a first period of time with at least a first light source and a second light source, such that during the first period of time the first and second light sources both illuminate the viewing location and the first light source illuminates the viewing location with a higher intensity than the second light source;
   acquiring a first image from light reflected from the viewing location during the first period of time using a camera, wherein the first and second light sources are located off-axis with respect to an optical axis of the camera;
   illuminating the viewing location during a second period of time with at least the first light source and the second light source, such that during the second period of time the first and second light sources both illuminate the viewing location and the second light source illuminates the viewing location with a higher intensity than the first light source;
   acquiring a second image from light reflected from the viewing location during the second period of time using the camera;
   obtaining combined data from at least the first and the second images, wherein the combined data comprises a reference location, a first glint location, and a second glint location; and
   determining a gaze direction based on the combined data.

2. The method of claim 1, wherein the first and the second light sources comprise infrared light-emitting diodes.

3. The method of claim 2, wherein the camera is an infrared camera.

4. The method of claim 3, wherein the first image is acquired by the infrared camera throughout the first period of time and the second image is acquired by the infrared camera throughout the second period of time.

5. The method of claim 1, wherein the viewing location corresponds to a position of an eye of a wearer of a head-mounted display (HMD).

6. The method of claim 5, wherein the reference location corresponds to a pupil location of the HMD wearer.

7. The method of claim 5, wherein the first and the second glint locations correspond to locations on the eye of the HMD wearer.

8. The method of claim 5, wherein the first glint location corresponds to a reflection off the cornea from the first light source and wherein the second glint location corresponds to a reflection off the cornea from the second light source.

9. The method of claim 5, wherein the gaze direction corresponds to a direction in which the HMD wearer is looking.

10. A wearable computing system, comprising:
    at least a first and a second light source, wherein the first and the second light sources are configured to illuminate a viewing location during a first period of time, such that during the first period of time the first and second light sources both illuminate the viewing location and the first light source illuminates the viewing location with a higher intensity than the second light source, and wherein the first and the second light sources are configured to illuminate the viewing location during a second period of time, such that during the second period of time the first and second light sources both illuminate the viewing location and the second light source illuminates the viewing location with a higher intensity than the first light source;
    a camera, wherein the camera is configured to acquire a first image from light reflected from the viewing location during the first period of time, wherein the camera is further configured to acquire a second image from light reflected from the viewing location during the second period of time, and wherein the first and second light sources are located off-axis with respect to an optical axis of the camera; and
    a computer, wherein the computer is configured to obtain combined data from at least the first and the second images, wherein the combined data comprises a reference location, a first glint location, and a second glint location, and wherein the computer is further configured to determine a gaze direction based on the combined data.

11. The wearable computing system of claim 10, wherein the first and the second light sources comprise infrared light-emitting diodes.

12. The wearable computing system of claim 11, wherein the camera is an infrared camera.

13. The wearable computing system of claim 12, wherein the first image is acquired by the infrared camera throughout the first period of time and the second image is acquired by the infrared camera throughout the second period of time.

14. The wearable computing system of claim 10, wherein the viewing location corresponds to a position of an eye of a wearer of a head-mounted display (HMD).

15. The wearable computing system of claim 14, wherein the reference location corresponds to a pupil location of the HMD wearer.

16. The wearable computing system of claim 14, wherein the first and the second glint locations correspond to locations on the eye of the HMD wearer.

17. The wearable computing system of claim 14, wherein the first glint location corresponds to a reflection off the cornea from the first light source and wherein the second glint location corresponds to a reflection off the cornea from the second light source.

18. The wearable computing system of claim 14, wherein the gaze direction corresponds to a direction in which the HMD wearer is looking.

19. A non-transitory computer readable medium having stored therein instructions executable by a computing device to cause the computing device to perform functions, the functions comprising:
controlling at least a first and a second light source to illuminate a viewing location during a first period of time, such that during the first period of time the first and second light sources both illuminate the viewing location and the first light source illuminates the viewing location with a higher intensity than the second light source;
controlling a camera to acquire a first image from light reflected from the viewing location during the first period of time, wherein the first and second light sources are located off-axis with respect to an optical axis of the camera;
controlling at least the first and the second light sources to illuminate the viewing location during a second period of time, such that during the second period of time the first and second light sources both illuminate the viewing location and the second light source illuminates the viewing location with a higher intensity than the first light source;
controlling the camera to acquire a second image from light reflected from the viewing location during the second period of time;
obtaining combined data from at least the first and the second images, wherein the combined data comprises a reference location, a first glint location, and a second glint location; and
determining a gaze direction based on the combined data.

20. The non-transitory computer readable medium of claim 19, wherein the first and the second light sources comprise infrared light-emitting diodes.

21. The non-transitory computer readable medium of claim 20, wherein the camera is an infrared camera.

22. The non-transitory computer readable medium of claim 21, wherein the first image is acquired by the infrared camera throughout the first period of time and the second image is acquired by the infrared camera throughout the second period of time.

23. The non-transitory computer readable medium of claim 19, wherein the viewing location corresponds to a position of an eye of a wearer of a head-mounted display (HMD).

24. The non-transitory computer readable medium of claim 23, wherein the reference location corresponds to a pupil location of the HMD wearer.

25. The non-transitory computer readable medium of claim 23, wherein the first and the second glint locations correspond to locations on the eye of the HMD wearer.

26. The non-transitory computer readable medium of claim 23, wherein the first glint location corresponds to a reflection off the cornea from the first light source and wherein the second glint location corresponds to a reflection off the cornea from the second light source.

27. The non-transitory computer readable medium of claim 23, wherein the gaze direction corresponds to a direction in which the HMD wearer is looking.

* * * * *